US012588958B2

(12) United States Patent
Graveley et al.

(10) Patent No.: US 12,588,958 B2
(45) Date of Patent: Mar. 31, 2026

(54) POSITION TRACKING DEVICE ASSEMBLIES AND COMPONENTS

(71) Applicant: Boston Scientific Scimed, Inc., Maple Grove, MN (US)

(72) Inventors: Andrew Graveley, Shoreview, MN (US); Daniel Foster, Lino Lakes, MN (US); George Duval, Sudbury, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 346 days.

(21) Appl. No.: 18/297,132

(22) Filed: Apr. 7, 2023

(65) Prior Publication Data

US 2023/0320797 A1 Oct. 12, 2023

Related U.S. Application Data

(60) Provisional application No. 63/374,107, filed on Aug. 31, 2022, provisional application No. 63/362,763, filed on Apr. 11, 2022.

(51) Int. Cl.
*A61B 34/00* (2016.01)
*A61B 34/20* (2016.01)
*A61B 34/30* (2016.01)

(52) U.S. Cl.
CPC .............. *A61B 34/30* (2016.02); *A61B 34/20* (2016.02); *A61B 34/73* (2016.02); *A61B 2034/2051* (2016.02); *A61B 2034/301* (2016.02)

(58) Field of Classification Search
None
See application file for complete search history.

(56) References Cited

U.S. PATENT DOCUMENTS

| | | | |
|---|---|---|---|
| 2017/0059361 A1* | 3/2017 | Nagarkar | ............... A61B 5/062 |
| 2018/0172420 A1 | 6/2018 | Hein et al. | |
| 2019/0217059 A1 | 7/2019 | Meyer et al. | |

FOREIGN PATENT DOCUMENTS

| | | | | |
|---|---|---|---|---|
| JP | 2007135881 A | * | 6/2007 | .......... A61B 8/0841 |
| JP | 2017148406 A | * | 8/2017 | ......... A61B 1/00098 |
| WO | WO-2021161002 A1 | * | 8/2021 | ............. A61B 34/74 |

\* cited by examiner

*Primary Examiner* — Sana Sahand

(74) *Attorney, Agent, or Firm* — Bookoff McAndrews PLLC

(57) ABSTRACT

An assembly of a medical device may comprise an elevator configured to raise and lower in order to adjust an orientation of an instrument inserted through a working channel of the medical device. The elevator may include a magnet. The assembly also may include a sensing element configured to measure a magnetic field of the magnet and to output a signal indicative of a configuration of the elevator.

12 Claims, 9 Drawing Sheets

POSITION TRACKING DEVICE ASSEMBLIES AND COMPONENTS

CROSS-REFERENCE TO RELATED APPLICATION(S)

This application claims the benefit of priority of U.S. Provisional Application No. 63/362,763, filed Apr. 11, 2022, and U.S. Provisional Application No. 63/374,107, filed Aug. 31, 2022, the entireties of which are incorporated by reference herein.

TECHNICAL FIELD

The disclosure relates generally to devices, systems, and methods for medical device assemblies and components. More specifically, aspects of the disclosure pertain to devices, systems, and/or methods that include position-tracking assemblies or position-tracking components of medical devices.

BACKGROUND

In a medical procedure, an operator may insert a medical device, such as a duodenoscope or other type of scope, into a body lumen of a subject. The operator may navigate a distal tip of the medical device to a desired location of the subject's anatomy. For example, in an endoscopic retrograde cholangiopancreatography ("ERCP") procedure, the operator may navigate a distal tip of the medical device (e.g., a distal tip of a duodenoscope) to a duodenum of the subject. The operator may then attempt to cannulate a papilla of the subject. Cannulation of the papilla may require repeated attempts at inserting a catheter, sphincterotome, or other instrument into the papilla orifice. Repeated attempts may cause trauma to a subject, potentially leading to pancreatitis. An imager (e.g., a camera) at a distal tip of the medical device may facilitate navigation of the instrument to cannulate the papilla, but the imager may be unable to visualize a trajectory of a bile duct, rendering it difficult for an operator to align the instrument for optimal insertion. For example, an imager may be limited to viewing areas that are within walls of the body lumen (e.g., within walls of the duodenum). Furthermore, the imager may be unable to convey information an operator desires in order to use an instrument for a procedure (e.g., a procedure in a tract such as one of the ducts accessed through the papilla). Therefore, a need exists for systems, devices, and/or methods that include position-tracking assemblies or position-tracking components of medical devices.

SUMMARY

Each of the aspects disclosed herein may include one or more of the features described in connection with any of the other disclosed aspects.

An assembly of a medical device may comprise an elevator configured to raise and lower in order to adjust an orientation of an instrument inserted through a working channel of the medical device. The elevator may include a magnet. The assembly also may include a sensing element configured to measure a magnetic field of the magnet and to output a signal indicative of a configuration of the elevator. Any of the aspects disclosed herein may include any of the following features, alone or in combination. The magnet may be diametrically magnetized. The magnet may be disposed in a recess of an axle of the elevator. The magnet may be approximately cylindrical. The magnet may rotate about a longitudinal axis of the magnet as the elevator is raised and lowered. The sensing element may be further configured to generate a signal indicative of an orientation of a distal tip of the medical device. The sensing element may be configured to measure an alternating external magnetic field in order to output the signal indicative of the orientation of the distal tip. The sensing element may be configured to measure a static magnetic field of the magnet. the sensing element may include a magnetoresistive sensor. The sensing element may be configured to measure a component of the magnetic field of the magnet that is along a sensing direction of the magnetoresistive sensor. An axis of the magnet may be configured to be offset from the sensing direction of the magnetoresistive sensor by a first amount in a first configuration of the elevator. The axis of the magnet may be configured to be offset from the sensing direction of the magnetoresistive sensor by a second amount in a second configuration of the elevator. The sensing element may be mounted on a substrate of a distal tip of the medical device. The magnet may be a permanent magnet. The sensing element may be a first sensing element, and the assembly may further comprise a second sensing element configured to measure a magnetic field of the magnet. The sensing element may be configured to measure a different magnitude of the magnetic field in a fully-raised configuration of the elevator than in a fully-lowered configuration of the elevator.

In another example, an assembly of a medical device may comprise: an elevator configured to raise and lower in order to adjust an orientation of an instrument inserted through a working channel of the medical device. The elevator may include a magnet or an elevator sensor. A sensing element may be configured to provide a signal indicative of a position or an orientation of a distal tip of the medical device. At least one of the sensing element or the elevator sensor may be configured to provide a signal indicative of a configuration of the elevator.

Any of the examples disclosed herein may include any of the following features, alone or in combination. The assembly may include the elevator sensor, and the elevator sensor may include a gyroscopic sensor. The assembly may include the magnet, and the sensing element may be configured to measure an alternating external magnetic field in order to output the signal indicative of the orientation of the distal tip. The sensing element may be configured to measure a static magnetic field of the magnet.

In another example, an assembly of a medical device may comprise: a distal tip including at least one sensing element configured to measure an alternating magnetic field and a static magnetic field. The alternating magnetic field may be generated externally to a subject. The distal tip may include a magnet that generates the static magnetic field. The at least one sensing element is configured to generate a signal that is indicative of (a) a position or an orientation of the distal tip and (b) a configuration of an elevator of the distal tip.

Any of the examples disclosed herein may include any of the following elements, alone or in combination. The elevator may include the magnet.

BRIEF DESCRIPTION OF THE DRAWINGS

The accompanying drawings, which are incorporated in and constitute a part of this specification, illustrate examples of this disclosure and together with the description, serve to explain the principles of the disclosure.

DETAILED DESCRIPTION

Figures 1A, 1B:
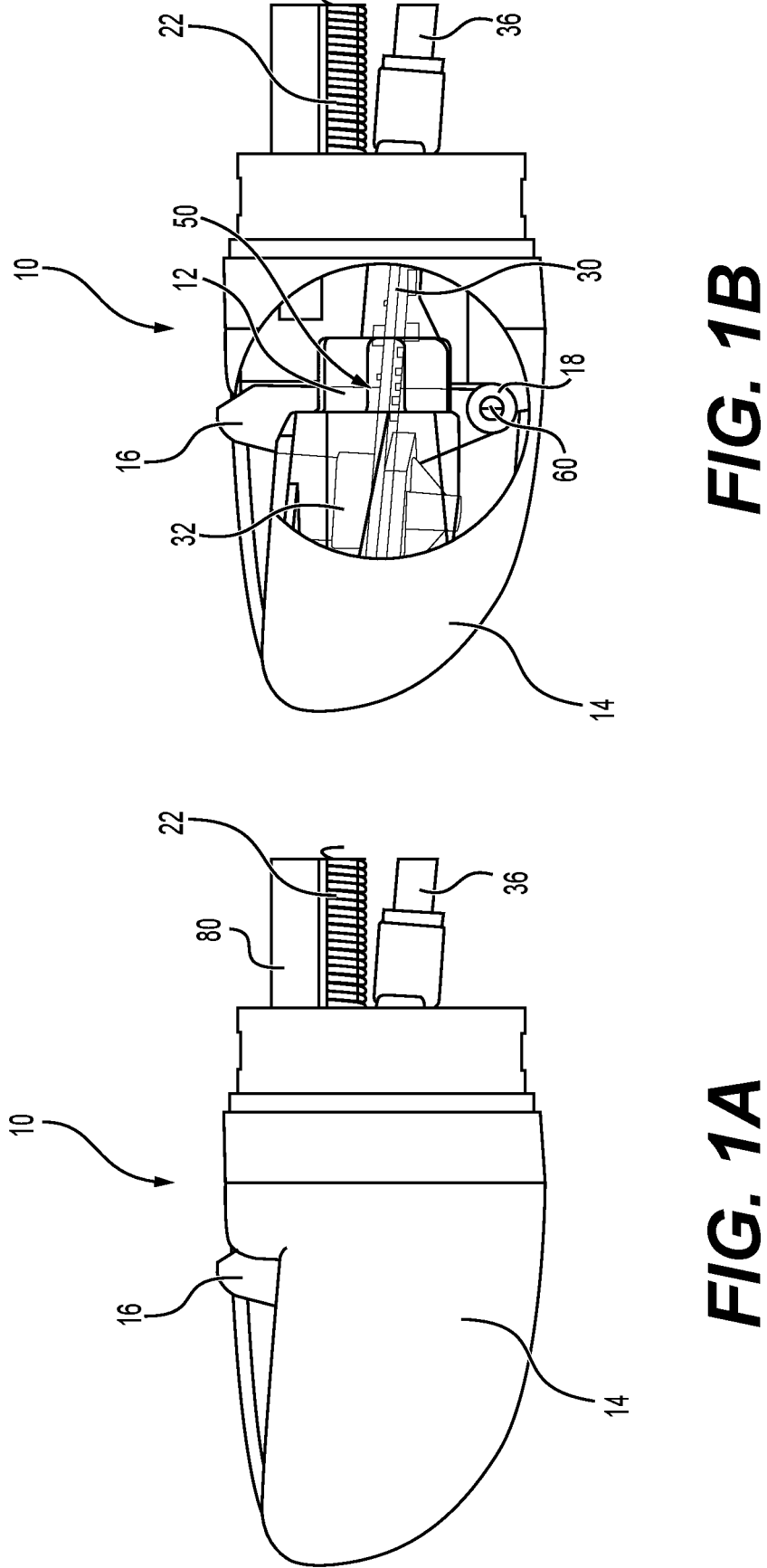
FIG. 1A depicts a side view of an exemplary distal tip of a medical device.
FIGS. 1B-1C depict partially transparent side views of the distal tip of FIG. 1A in first (FIG. 1B) and second (FIG. 1C) configurations of the distal tip.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator/toward a treatment site, and the term "proximal" refers to a direction toward an operator. The term "approximately," or like terms (e.g., "substantially"), includes values +/−10% of a stated value.

A distal assembly of a medical device, such as a duodenoscope, may include an elevator for adjusting an orientation of an instrument inserted through a working channel of the medical device. The elevator may include a magnet, such as a permanent magnet, disposed thereon or therein, or the elevator itself may be a permanent magnet. The distal assembly may also include a substrate (e.g., a circuit board), which may have mounted thereon elements such as imaging elements and/or lighting elements. Imaging elements may include one or more image sensors or cameras. Lighting elements may include one or more (e.g., two) light emitting diodes ("LEDs") or fiber optic light guides. The circuit board may also have mounted thereon one or more position-sensing systems. For example, a position-sensing system may include one or more magnetoresistance ("MR") sensors (i.e., MR elements), one or more diodes (e.g., two diodes), and/or one or more capacitors (e.g., one capacitor). For example, the MR sensors may include tunneling magnetoresistance ("TMR") sensors (i.e., TMR elements). The position-sensing system may measure a position and/or orientation of the elevator and/or a position and/or orientation of the distal tip assembly, including a position and/or orientation of those components relative to an external magnetic field generator. For example, the position-sensing system may measure a magnetic field emitted by the magnet of the elevator, and a controller may utilize the measurements to determine a position and/or orientation of the elevator. Information about the position and/or orientation of the elevator may be presented to an operator of the medical device to facilitate positioning of an instrument inserted through the working channel of the medical device.

Due to elasticity in a shaft of the medical device and a mechanical control system (e.g., actuator) for controlling the elevator, a position of an elevator control (e.g., lever or knob) may not reliably reflect a position of the elevator. This may be particularly problematic when using the elevator to adjust a position of a large-diameter instrument, because increased force may be applied to the actuator to displace the actuator, but only limited movement of the elevator itself may occur. Thus, absent the position-sensing system of the disclosure, an operator may rely on images from a camera (e.g., a video feed) to observe a position of the instrument as the elevator is moved. The camera may provide incomplete information about the instrument position, as well as incomplete information about the anatomy surrounding the medical device.

In the case of a digital or robotic procedure (or a procedure performed by a human operator), feedback about a position of an elevator may be desired to determine an angle of an accessory instrument and to aid with bile duct alignment. However, as discussed above, a position of an actuator controlling the elevator may not accurately reflect a position of the elevator, and an orientation of the instrument inside the elevator will not be precisely known if using a monocular camera view. The disclosed position-sensing system may address this problem by providing information about a position of the distal tip assembly and/or the elevator. With respect to a human operator (or a robotic procedure), the position-sensing system may enable use of an augmented camera view or an augmented three-dimensional ("3D") view in which an operator may see a trajectory of the instrument, a location of the papilla, and/or a trajectory of the bile duct in real time, and/or in the same coordinate system. The position-sensing system may assist cannulation of the papilla with minimal changes to a current ERCP workflow. Thus, the disclosed position-sensing system may address one or more problems in the art. For example, the position and/or orientation information may facilitate cannulation of a papilla of a subject and/or positioning of an instrument being manipulated by the elevator.

Figures 1C, 2:
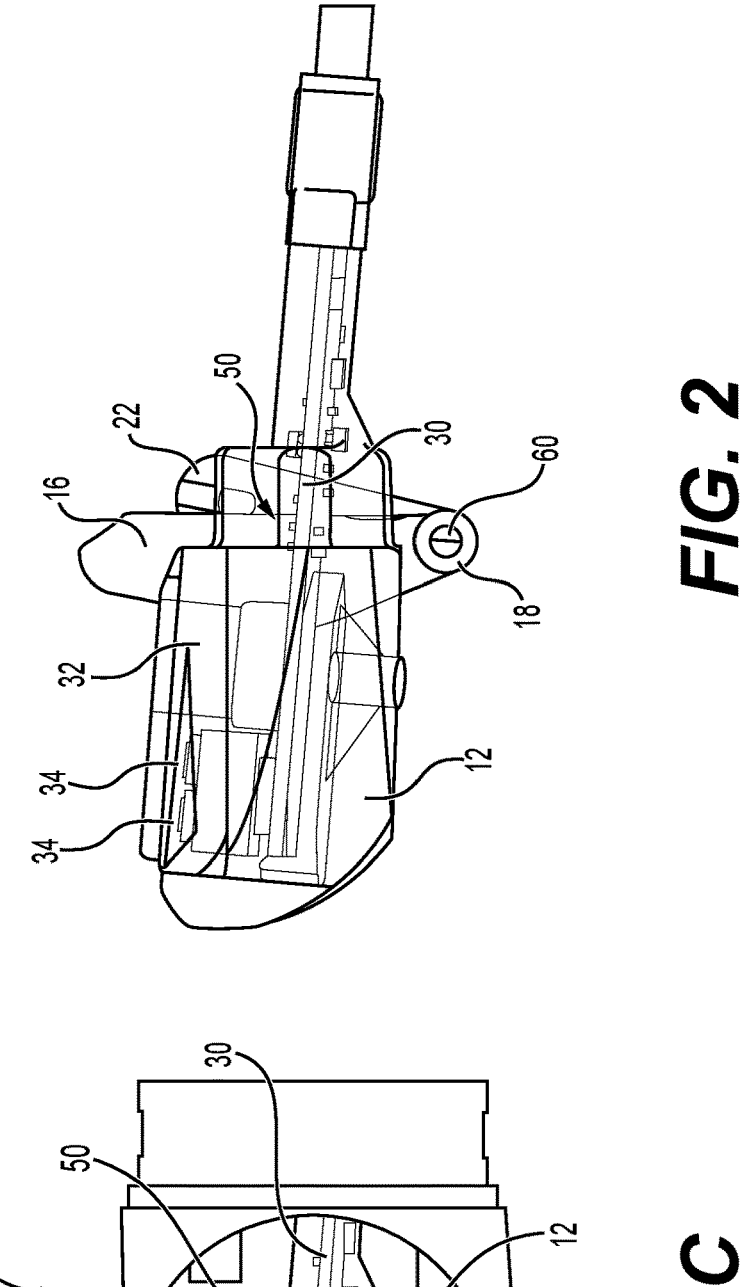
FIG. 2 depicts a side view of a portion of the exemplary distal tip of FIGS. 1A-1C.

FIGS. 1A-1C are side views that depict aspects of a distal tip assembly 10 for use with a medical device, such as medical device 100 (FIG. 5), discussed below. Distal tip assembly 10 may include a core 12 and a cover 14. Core 12 may include elements of distal tip assembly 10 mounted therein or thereon, and cover 14 may be disposed about core 12. In FIGS. 1A and 1B, portions of cover 14 are depicted as transparent, in order to show features of distal tip assembly 10. FIG. 2 depicts core 12 and elements of distal tip assembly 10, without cover 14.

Figure 3C:
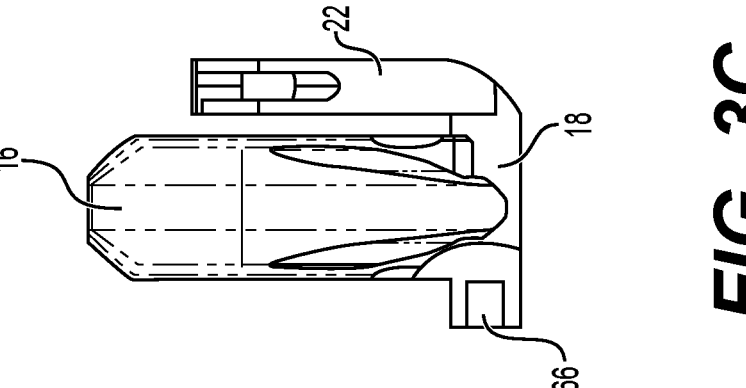
FIGS. 3A-3C depict views of an exemplary elevator of the exemplary distal tip of FIGS. 1A-1C.
Figure 3B:
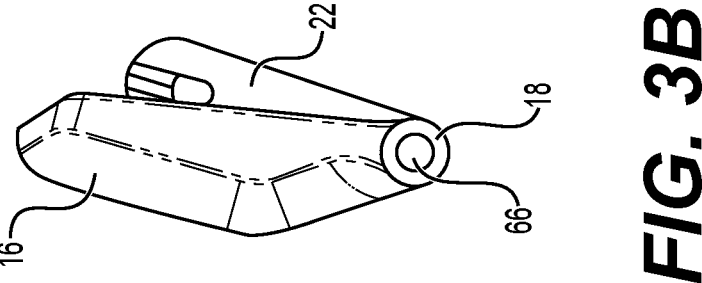
Figure 3A:
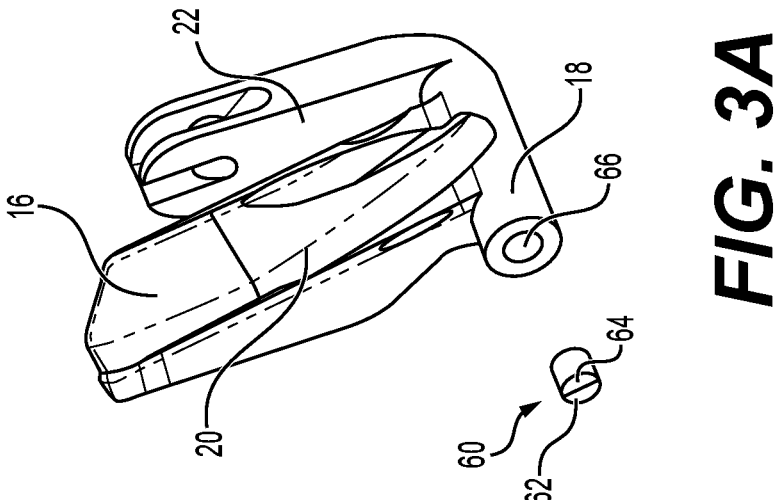

Distal tip assembly 10 also may include an elevator 16. Elevator 16 may have any of the properties of elevators, pivot stands, swing stands, or similar structures known in the art. FIGS. 3A-3C depict aspects of an exemplary elevator 16. FIG. 3A shows a perspective view of elevator 16, FIG. 3B shows a side view of elevator 16, and FIG. 3C shows a plan view of elevator 16. Elevator 16 may be rotatable about an axle 18. Axle 18 may be rotatably retained within distal tip assembly 10 (e.g., within cover 14 or another portion of distal tip assembly 10). Elevator 16 may include a guide surface 20 for contacting a medical instrument. Elevator 16 also may include an arm 22 for connecting to a control mechanism, which may include a wire (not shown) of a Bowden cable 24 (FIGS. 1A and 1B). An operator may use an actuator (e.g., actuator 112 of medical device 100, shown in FIG. 5 and discussed below) of a handle (e.g., handle 110 of medical device 100, shown in FIG. 5 and discussed below) in order to move the wire proximally or distally. A distal end of the wire may be attached to arm 22. Proximal movement of the wire may thus cause elevator 16 to rotate to a first, raised configuration (FIGS. 1A and 1B). Distal movement of the wire may cause elevator 16 to rotate to a second, lowered configuration (FIG. 1C).

Figure 4A:
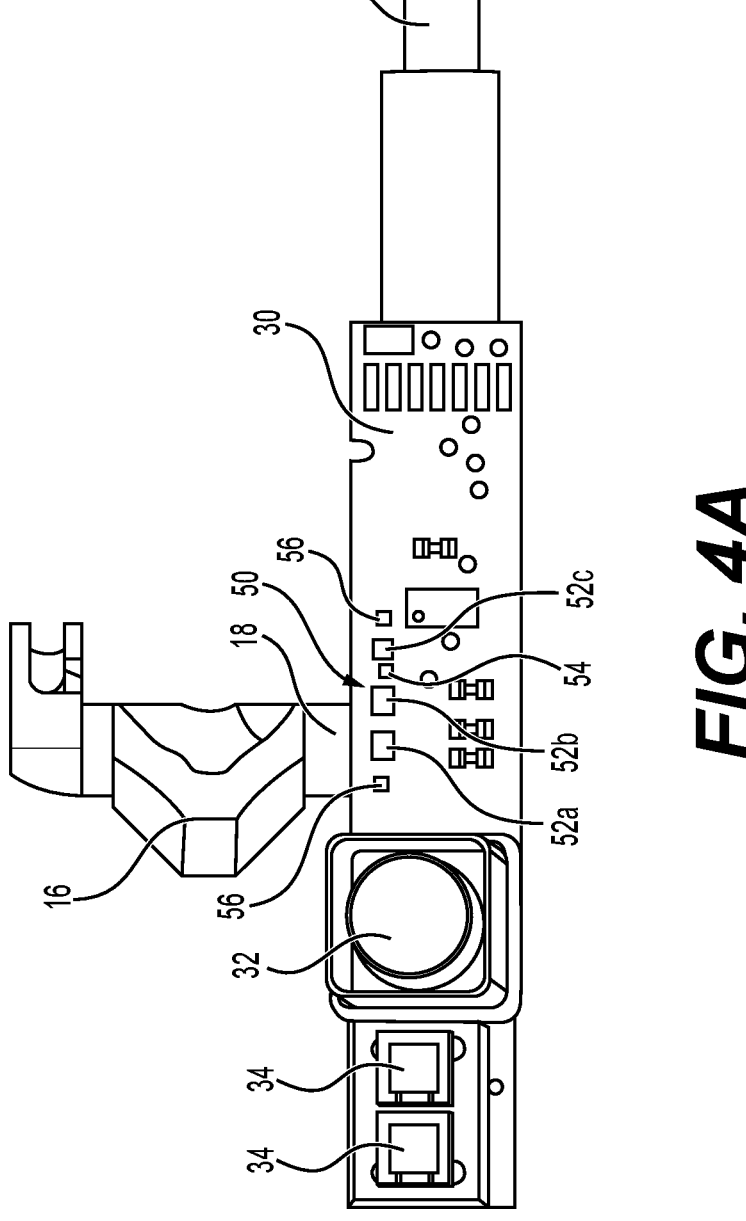
FIGS. 4A-4C depict plan (FIG. 4A), side (FIG. 4B), and perspective (FIG. 4C) views of the elevator of FIGS. 3A-3C and electronic components of the exemplary distal tip of FIGS. 1A-1C.
Figure 4C:
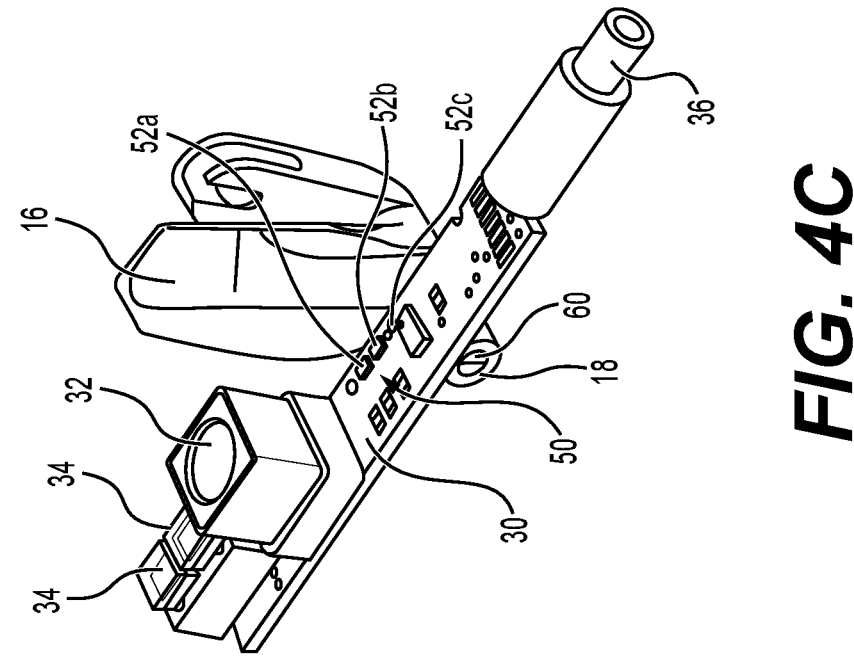
Figure 4B:
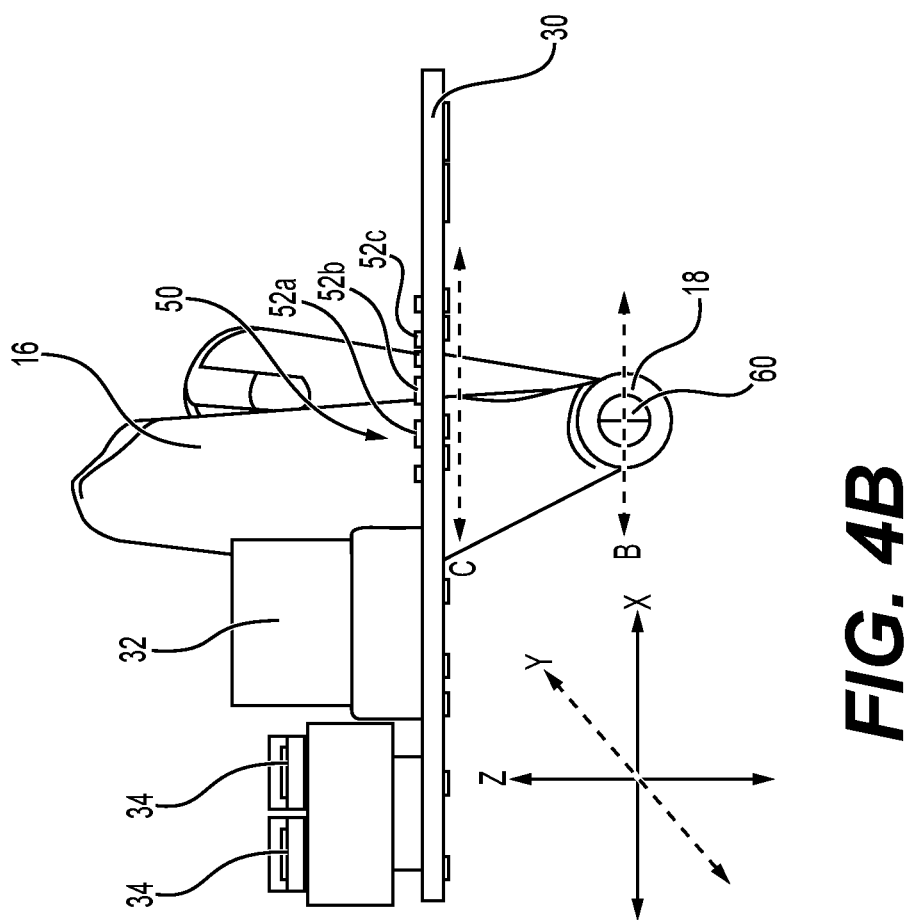

As shown in FIGS. 1A-1C, substrate 30 (e.g., a rigid or flexible circuit board or other type of board) may be disposed at least partially within or on core 12. In examples, substrate 30 is rigid and includes multiple layers. Substrate 30 and its elements are shown with particular detail in FIGS. 4A-4C. Each of FIGS. 4A-4C depicts substrate 30 and elevator 16, with elevator 16 in a raised configuration. Although core 12 and cover 14 are not depicted in FIGS. 4A-4C, substrate 30 and elevator 16 are depicted in the positions that they would have within core 12/cover 14 in distal tip assembly 10. FIG. 4A shows a plan view of substrate 30 and elevator 16 in a raised position, FIG. 4B shows a side view of substrate 30 and elevator 16, and FIG. 4C shows a perspective view of substrate 30 and elevator 16. Aspects of substrate 30 may also be seen in FIGS. 1B, 1C, and 2. Electronic components may be mounted on substrate 30. For example, an imaging device 32 (e.g., a camera, including, e.g., one or more lenses and/or an imager) may be mounted to substrate 30 by any suitable method (e.g., wire bonding, surface mount assembly, electro mechanical assembly, and/or plated through-hole technology). Camera 32 may be configured to take video and/or still images. Imaging device 32 may provide a signal to a display (e.g., a display of a controller 130, discussed below with respect to FIG. 5, or a separate display), so that an operator may view a visual image provided by imaging device 32 while navigating distal tip assembly 10 through a body of a subject.

As shown particularly in FIGS. 2 and 4A-4C, one or more lighting elements 34 (e.g., light emitting diodes ("LEDs"), fibers, or other elements for providing light) may be mounted to substrate 30 by any suitable method (e.g., wire bonding, surface mount assembly, electro mechanical assembly, and/or plated through-hole technology). Although two lighting elements 34 are depicted in FIG. 2, any suitable number of lighting elements 34 may be utilized (e.g., one, three, four, or more lighting elements 34). Alternatively, lighting elements 34 and imaging device 32 may be combined into a single device. A conduit 36 may contain one or more wires or cables that attach to substrate 30 or elements mounted on substrate 30, in order to transmit power and/or signals to substrate 30 and/or elements mounted on substrate 30.

As shown in FIGS. 2 and 4A-3C, lighting elements 34 may be disposed distally of imaging device 32. For example, lighting elements 34 may be disposed at a distalmost end of substrate 30. Lighting elements 34 may be arranged approximately along a longitudinal axis of distal tip assembly 10/substrate 30. One lighting element 34 may be distal of another lighting element 34, and lighting elements 34 may be arranged linearly. Imaging device 32, and each of lighting elements 34 may be directly adjacent to one another, or there may be gap(s) between imaging devices 32 and/or lighting elements 34.

As depicted in FIGS. 1A-1C and 2, distal tip assembly 10 may be "side-facing." In other words, features of distal tip assembly 10 (e.g., imaging device 32 and lighting elements

34) may face radially outward (i.e. to a side of distal tip assembly 10), transverse (e.g., approximately perpendicularly) to a longitudinal axis of distal tip assembly 10 (and a shaft of a medical device such as shaft 114 of medical device 100, described below). This disclosure also encompasses other configurations of distal tip 42. For example, distal tip assembly 10 may be "forward facing" (i.e., distal-facing). An instrument exiting a distal opening (not shown) of a working channel (e.g., working channel 116 of medical device 100, described below) also may face radially outward. An operator may raise/lower elevator 16 in order to change an orientation and/or of the instrument. As used herein, the word "orientation" includes a rotational disposition of an element (e.g., how an element has been rotated about an axis). As used herein, the word "position" includes a location of an element in a coordinate system. It is possible for an element to change position and orientation at the same time.

Elements of a position sensing system 50 may also be disposed on substrate 30 and may be mounted according to any of the techniques described above for imaging device 32 and lighting elements 34. Position sensing system 50 may incorporate any of the features described in U.S. patent application Ser. No. 15/846,846, filed Dec. 19, 2017, issued as U.S. Pat. No. 10,782,114, on Sep. 22, 2020, or U.S. patent application Ser. No. 16/248,352, filed Jan. 15, 2019, issued as U.S. Pat. No. 11,141,567 on Oct. 12, 2021, the entireties of which are incorporated herein by reference. Position sensing system 50 may include one or more magnetic field sensing elements 52a, 52b, 52c disposed on substrate 30. For example, as shown in FIGS. 4A-4C, three magnetic field sensing elements 52a, 52b, 52c may be disposed on substrate 30. Any alternative number of sensors may be utilized, and the three magnetic field sensing elements 52a, 52b, 52c depicted are exemplary only. Magnetic field sensing elements 52a, 52b, 52c may have the capability of measuring static magnetic fields, which may facilitate tracking a position of elevator 16, as discussed below. Magnetic field sensing elements 52a, 52b, 52c also may have the capability of measuring alternating magnetic fields, which may facilitate tracking a position/orientation of distal tip assembly 10, as discussed below. Magnetic field sensing elements 52a, 52b, 52c may include, for example, MR elements, such as TMR elements, anisotropic-magneto-resistive sensing elements, giant magneto-resistive sensing elements, colossal magneto-resistive sensing elements, extraordinary magneto-resistive sensing elements, or semiconductor magneto-resistive elements. Additionally or alternatively, magnetic field sensing elements 52a, 52b, 52c may include one or more flux gates or hall-effect sensing elements. Although TMR sensors and properties of TMR sensors may be referred to herein, it will be appreciated that any type of magnetic field sensor may be utilized, including those listed above. Magnetic field sensing elements 52a, 52b, 52c may have any properties of magnetic field sensing elements (including, e.g., MR elements, such as TMR elements) known in the art. For example, magnetic field sensing elements 52a, 52b, 52c may include a fixed layer, a tunnel layer, and a free layer. A resistance may change when the free layer is aligned with the fixed layer.

In some examples, as shown in 4A-4C, magnetic field sensing elements 52a, 52b, 52c may be arranged in a dual-axis, six-degree-of-freedom arrangement. In such an arrangement, magnetic field sensing elements 52a, 52b may be oriented such that their primary sensing direction C (FIG. 4B) is aligned with (approximately parallel to) a longitudinal axis of distal tip assembly 10 and substrate 30, as shown in FIG. 4B. Magnetic field sensing elements 52a, 52b may together generate one signal. By way of non-limiting example, a full-Wheatstone bridge configuration may be utilized by the two magnetic field sensing elements 52a, 52b. The third magnetic field sensing element 52c may be arranged such that its primary sensing direction is transverse (e.g., approximately orthogonal/perpendicular) to the longitudinal axis. In some non-limiting examples, a half-Wheatstone bridge configuration may be utilized by magnetic field sensing element 52c. The Wheatstone bridges may have any characteristics of Wheatstone bridges known in the art. Magnetic field sensing elements 52a, 52b, 52c may detect an orientation/position of distal tip assembly 10 and may transmit signals indicative of the orientation/position of distal tip assembly 10. A controller (such as controller 130 of FIG. 5, described below) may receive the signals and may calculate positioning of distal tip assembly 10 using the measurements from magnetic field sensing elements 52a, 52b, 52c across the primary sensing direction (from magnetic field sensing elements 52a, 52b) and the direction transverse (e.g., orthogonal) to the primary sensing direction (from magnetic field sensing element 52c).

Position sensing system 50 may also optionally include a capacitor 54 (labeled in FIG. 4A) for reducing noise in a voltage supplying position sensing system 50. For example, capacitor 54 may function as a decoupling capacitor, acting as a low-pass filter for any electromagnetic interference ("EMI") on the supply voltage. Position sensing system 50 may also optionally include one or more diodes 56 (labeled in FIG. 4A). Diodes 56 may provide high voltage protection, such as electrostatic discharge ("ESD") protection. Diodes 56 may prevent damage to magnetic field sensing elements 52a, 52b, 52c from static discharge. Diodes 56 may additionally or alternatively provide protection to aspects of camera 32.

Other components, such as one or more integrated circuits also may be positioned on substrate 30. In examples, an integrated circuit may digitize and/or multiplex signals from elements of substrate 30, including, for example, elements of position sensing system 50. Such integrated circuit(s) may reduce a number of wires required to pass through conduit 36.

Elevator 16 may include a magnet 60, which may include a permanent magnet. As shown particularly in FIG. 3A, magnet 60 may have an approximately cylindrical or disc shape. Magnet 60 may be diametrically magnetized, such that an axis of magnet 60 (shown in FIG. 4B, a line B extending between the south pole and the north pole of magnet 60) may extend along a diameter of a cross-section of magnet 60, where the cross-section is perpendicular to a longitudinal axis of magnet 60. As shown in FIG. 3A, magnet 60 may include a first polarized portion 62 (e.g., a north polarized portion) and a second polarized portion 64 (e.g., a south polarized portion). As shown particularly in FIG. 3A, each of first polarized portion 62 and second polarized portion 64 may have an approximately semicircular cross-sectional shape, where the cross-section is perpendicular to the longitudinal axis of magnet 60. Magnet 60 may be made from any suitable material. For example, magnet 60 may include a neodymium magnet (e.g., a grade N52 neodymium magnet) or another type of rare earth magnet. Magnet 60 may be coupled to elevator 16 in any suitable fashion and may be disposed on or within various portions of elevator 16.

As shown in FIGS. 3A-3C, axle 18 of elevator 16 may have a recess 66 formed therein. Recess 66 may have an approximately cylindrical shape. A shape of recess 66 may complement a shape of magnet 60. Recess 66 may be formed in an end of axle 18 that is opposite to arm 22 (a side of axle 18 that is closer to substrate 30, including position sensing system 50). In other words, recess 66 may be formed in the end of axle 18 that faces in a radially inward direction of distal tip assembly 10. Magnet 60 may be disposed within recess 66. A material of magnet 60 may be biocompatible. For example, magnet 60 may lack a nickel coating, as subjects may be allergic to nickel. Additionally or alternatively, magnet 60 may be fully encased within elevator 16 and/or a medical grade epoxy. For example, magnet 60 may be disposed within recess 60, and recess 60 may be covered with medical grade epoxy. Magnet 60 also may include a material or other properties that enable magnet 60 to withstand sterilization procedures (e.g., heat) to which a medical device (e.g., medical device 100) having distal tip assembly 10 may be subject.

Position sensing system 50 may be configured to measure changes in a magnetic field of magnet 60 as elevator 16 moves between a raised configuration and a lowered configuration (i.e., rotates about axle 18 of elevator 16). For example, as discussed in further detail below, one or more of magnetic field sensing elements 52a, 52b, 52c may measure a magnetic field of magnet 60, including changes in the magnetic field, as elevator 16 moves. In the example shown in FIGS. 1A-4C, magnetic field sensing elements 52a, 52b (the magnetic field sensing elements having their primary axes aligned along the longitudinal axis of distal tip assembly 10) may measure the magnetic field of magnet 60. For example, the north and south poles of the depicted diametrically magnetized magnet 60 may rotate along with axle 18, causing the magnetic field of magnet 60 to change as elevator 16 moves.

In an example, in a first configuration of elevator 16 (e.g., a fully raised configuration of elevator 16), axis B of magnet 60 may be offset from primary sensing direction C of magnetic field sensing elements 52a, 52b by approximately 0 degrees. In a second configuration of elevator 16 (e.g., a fully lowered configuration of elevator 16), axis B of magnet 60 may be offset from primary sensing direction C of magnetic field sensing elements 52a, 52b by approximately 63 degrees. A distance between (a) a top of magnet 16 in FIG. 4B and (b) magnetic field sensing elements 52a, 52b (e.g., a midpoint between magnetic field sensing elements 52a, 52b) may be approximately constant (e.g., approximately 4.1 mm along a z-axis of FIG. 4B and/or approximately 1 mm along a y-axis of FIG. 4B, or any other suitable distance). The distances and angles provided above are merely exemplary, and any suitable distances and angles may be utilized.

Although a cylindrical, diametrically magnetized magnet 60 is depicted in FIGS. 1B-3A, magnet 60 may have any suitable shape and arrangement of poles. Magnet 60 may be suitable for use with elevator 16 if, as elevator 16 moves between raised and lowered configurations, a magnetic field emitted by magnet 60 changes. Although magnet 60 is shown as being disposed within axle 18, magnet 60 may alternatively be disposed on or within other portions of elevator 16. Additionally or alternatively, a portion or an entirety of elevator 16 may include a magnet. In an example, elevator 16 may be formed of a single, monolithic piece and may be magnetic. A type of magnet 60 (e.g., shape, pole configuration, material, etc.) may be chosen based on a location at which magnet 60 is disposed on or in elevator 16. A strength of magnet 60 may be chosen so that the magnetic field of magnet 60 may be measured by magnetic field sensing elements 52a, 52b, 52c, without saturating position sensing system 50. For example, it may be desirable for magnet 60 to emit a strong magnetic field, but not so strong a magnetic field that the magnetic field saturates position sensing system 50. Relatedly, relative positions of elements of position sensing system 50 (e.g., one or more magnetic field sensing elements 52a, 52b, 52c) and magnet 60 (including, e.g., a distance between one or more magnetic field sensing elements 52a, 52b, 52c and magnet 60) may be chosen so as to avoid saturation of position sensing system 50 while providing for a strong magnetic field from magnet 60 at a position of one or more magnetic field sensing elements 52a, 52b, 52c and magnet 60.

Elements of position sensing system 50 may be disposed in any position on substrate 30 with close enough proximity to magnet 60 and with sufficient distance from high magnetic permeability materials that could alter the field of magnet 60. For example, with reference to the coordinates of FIG. 4B, a portion or an entirety of magnet 60 may be generally below a portion of substrate 30 having magnetic field sensing elements 52a, 52b, and/or 52c. In one example, magnet 60 may be approximately 4.1 mm away from magnetic field sensing elements 52a, 52b, and/or 52c. A small size of elements of position sensing system 50 may allow positioning of the elements on open areas of substrate 30, without otherwise reconfiguring substrate 30. Thus, position sensing system 50 may be added to existing devices with minimal design modifications. Because magnetic field sensing elements 52a, 52b may be used to generate one signal, magnetic field sensing elements 52a, 52b may be positioned on substrate 30 such that a point midway between elements 52a, 52b is the point at which the magnetic field of magnet 60 will be measured. For example, magnet 60 may be generally below the midpoint between magnetic field sensing elements 52a, 52b in the coordinate system of FIG. 4B (i.e., a coordinate system in which camera 32 and/or lighting elements 34 face approximately upward). For example, magnet 60 may be approximately 4.1 mm below the midpoint, in a z-direction of FIG. 4B. Magnet 60 may be offset radially from magnetic field sensing elements 52a, 52b or may be directly below magnetic field sensing elements 52a, 52b. In one example, as shown in FIGS. 4A-4C, magnet 60 may be offset from magnetic field sensing elements 52a, 52b by approximately 1 mm in a y-direction of FIG. 4B. The distance between magnet 60 and the midpoint between magnetic field sensing elements 52a, 52b is merely exemplary, and any suitable arrangement may be utilized.

Alternate configurations (not shown) of substrate 30 and magnet 60 may allow for measurement of stronger regions of a magnetic field of magnet 60, along a dipole axis of magnet 60. For example, one or more magnetic field sensing elements 52a, 52b, 52c may be configured to sense in the z-direction of FIG. 4B or other directions. Alternatively or additionally, one or more magnetic field sensing elements 52a, 52b, 52c may measure along different directions from one another. Alternatively or additionally, magnet 60 may be moved so that axis B of magnet 60 (see FIG. 4B) aligns with one or more magnetic field sensing elements 52a, 52b, 52c (i.e., is not offset along the z-axis of FIG. 4B). The above alternate configurations are merely exemplary, and other configurations may be utilized.

Position sensing system 50 may have other configurations within the scope of the disclosure. For example, a tri-axis configuration may be utilized for magnetic field sensing elements 52a, 52b, 52c, in which each of the magnetic field sensors is arranged so that its primary sensing direction is aligned with a different axis (e.g., the primary sensing directions of magnetic field sensing elements 52a, 52b, 52c are aligned orthogonally to one another). For example, magnetic field sensing element 52a may have a primary sensing direction of the X-axis. Magnetic field sensing element 52b may have a primary sensing direction of the Y-axis, and magnetic field sensing element 52c may have a primary sensing direction of the Z-axis. In such a tri-axis configuration, each of the magnetic field sensing elements 52a, 52b, 52c, may utilize a half-Wheatstone bridge configuration. In another example, only two magnetic field sensors (e.g., magnetic field sensing elements 52a, 52b) may be utilized to measure six degrees of freedom, with each of magnetic field sensing elements 52a, 52b having a half-Wheatstone bridge configuration (or a full Wheatstone bridge configuration). In a further example, two magnetic field sensors (e.g., magnetic field sensing elements 52a, 52b) may be used to measure five degrees of freedom. In such an example, position sensing system 50 may be unable to measure roll. In an additional example, a single magnetic field sensing element 52a may use a half Wheatstone bridge to measure five degrees of freedom.

All or a subset of magnetic field sensing elements 52a, 52b, 52c may be used to measure a magnetic field of magnet 60, depending on a configuration of position sensing system 50. For example, three magnetic field sensing elements (e.g., 52a, 52b, 52c, two magnetic field sensing elements (e.g., 52a, 52b, as shown in FIGS. 1A-4C), or one magnetic field sensing element (e.g., 52a) may be used to measure a magnetic field of magnet 60. In the configuration shown in FIGS. 1A-4C, because each magnetic field sensing element 52a, 52b may measure a magnetic field along only a single axis (and magnetic field sensing elements 52a, 52b have the same sensing axis), magnetic field sensing elements 52a, 52b may not measure fields that are normal to a surface of substrate 30, on which magnetic field sensing elements 52a, 52b are mounted.

The above examples are merely illustrative and other configurations of magnetic field sensors may be utilized. A system that utilizes three magnetic field sensing elements 52a, 52b, 52c in a dual-axis, six-degree-of-freedom arrangement, as shown in FIGS. 1A-4C may be beneficial due to an ability to measure six degrees of freedom, as well as a position/orientation of elevator 16. Alternative arrangements may also be used for lighting elements 34 and imaging element 32.

Distal tip assembly 10 may also include components in addition to or in the alternative to the components described above. For example, distal tip assembly 10 also may include additional or alternative sources of lighting and/or additional or alternative imaging components (e.g., additional cameras). Distal tip assembly 10 may also include additional types of sensors, such as moisture sensors, temperature sensors, pressure sensors, or other types of sensors, which may be useful during a medical procedure.

Figure 5:
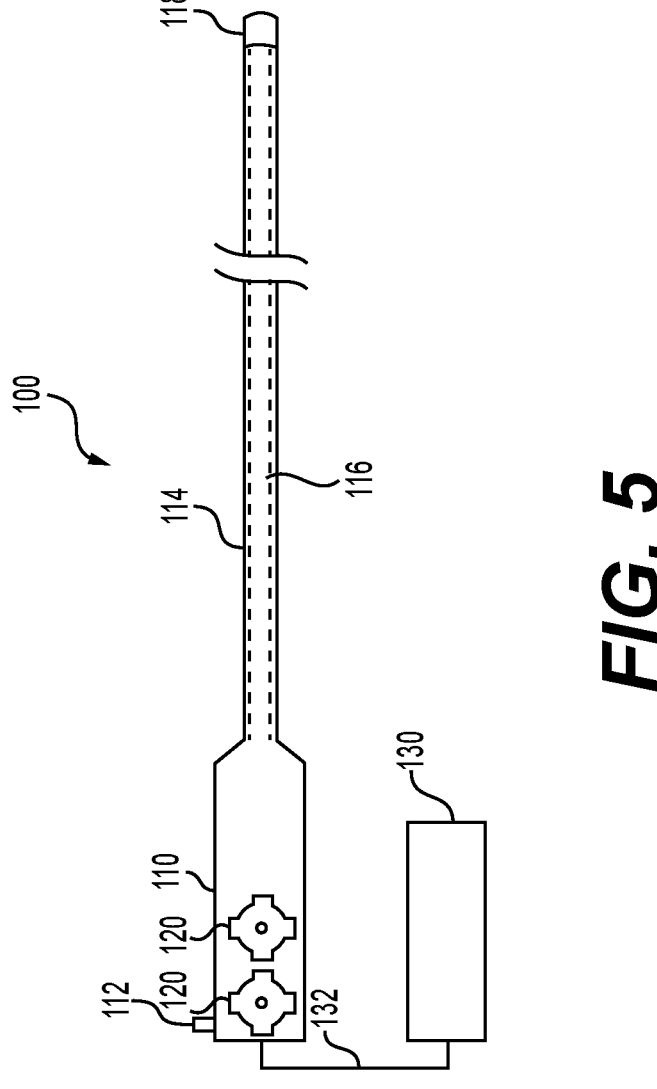
FIG. 5 depicts an exemplary medical device, which may include the exemplary distal tip of FIGS. 1A-1C.

FIG. 5 depicts exemplary medical device 100. In examples, medical device 100 may include a duodenoscope or an endoscope. Although the disclosure may refer at different points to a duodenoscope or an endoscope, it will be appreciated that, unless otherwise specified, bronchoscopes, endoscopes, gastroscopes, endoscopic ultrasonography ("EUS") scopes, colonoscopes, ureteroscopes, laparoscopes, cytoscopes, aspiration scopes, sheaths, catheters, or any other suitable delivery device or medical device may be used in connection with the elements and assemblies described herein. Exemplary medical device 100 may include handle 110 and shaft 114. Shaft 114 may extend distally from handle 110. Shaft 114 may terminate distally in a distal tip 118, which may have any of the properties of distal tip assembly 10. Working channel 116 may extend from handle 110, through shaft 114, to an opening (not shown) of distal tip 118. Handle 110 may include actuators and/or other controls. For example, handle 110 may include actuator 112. Actuator 112 may include, for example, a lever or other type of actuator (e.g., button, slider, knob, or joystick). Actuator 112 may be actuated to raise and/or lower elevator 16. Handle 110 may also include actuators 120. Actuators 120, may include, for example, knobs or other types of actuators (e.g., buttons, sliders, levers, or joysticks). Although FIG. 5 shows two actuators 120 (e.g., one actuator 120 for up/down movement and one actuator 120 for left/right movement), any suitable number of actuators 120 may be utilized. Actuators 120 may be utilized to steer (e.g., articulate) a distal portion of shaft 114. An umbilicus 132 may extend between medical device 100 and controller 130. Umbilicus 132 may transmit power, signals, air, water, suction, or other fluids between controller 130 and medical device 100. In one example, air/water and/or suction provided by controller 130, via umbilicus 132, may be delivered to distal tip assembly 10 via a conduit 80 (see FIG. 1A).

Figure 6B:
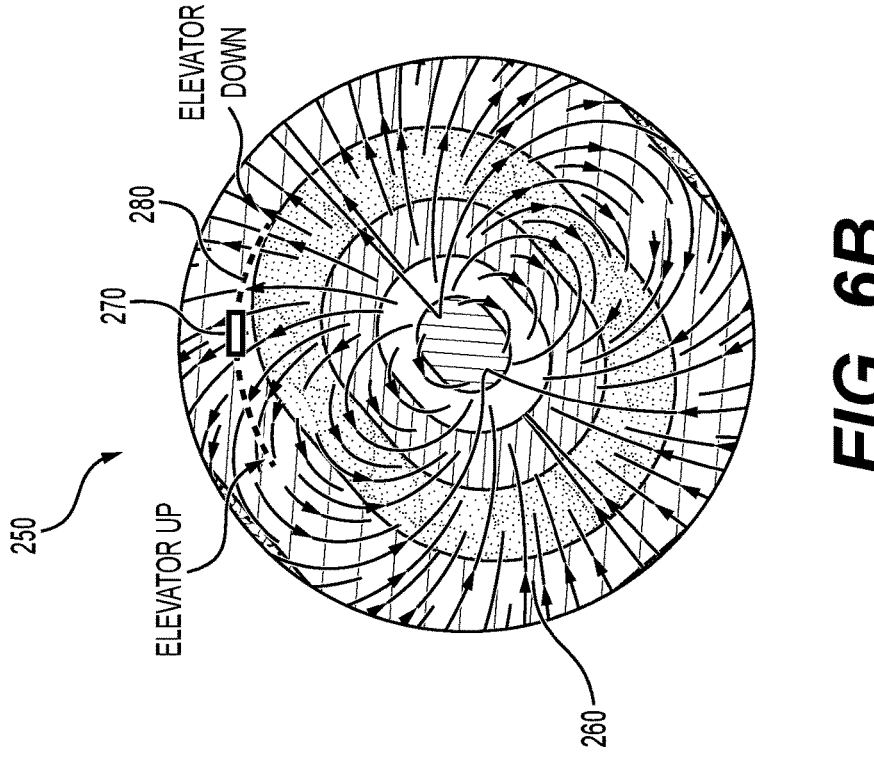
FIGS. 6A and 6B depict exemplary magnetic fields of a magnet of the exemplary distal tip of FIGS. 1A-1C.
Figure 6A:
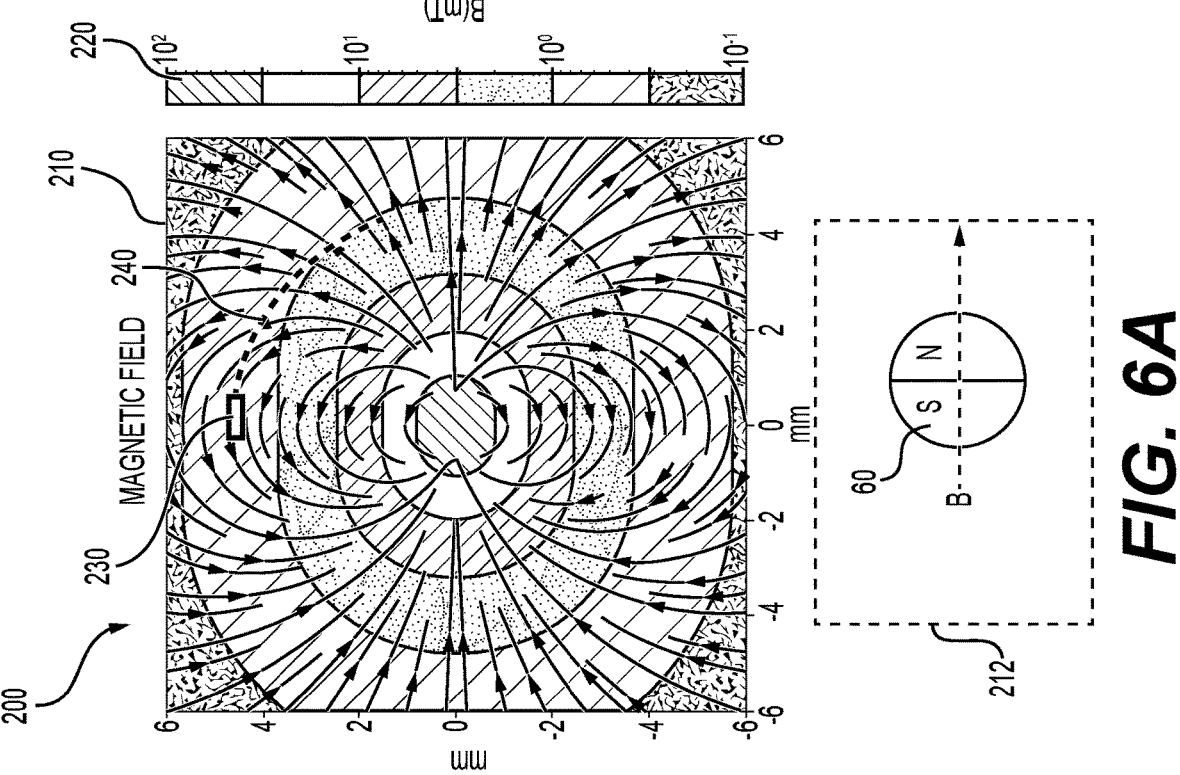

FIGS. 6A and 6B depict magnetic fields of a diametrically-magnetized cylindrical magnet 60 and a position of a magnetic field sensing element (e.g., one or more of magnetic field sensing elements 52a, 52b, 52c), relative to magnet 60. FIG. 6A is depicted from a frame of reference of magnet 60. In particular, the frame of reference of FIG. 6A depicts a south pole of magnet 60 to the left side, and a north pole of magnet 60 to the right side, as shown in inset 212 of FIG. 6A. Inset 212 depicts a cross-sectional view of magnet 60, with axis B extending from the south pole of magnet 60 to the north pole of magnet 60. Although the fields depicted in FIGS. 6A and 6B pertain to a diametrically-magnetized cylindrical magnet 60, similar diagrams may be created for other types of magnets, and the steps described below for calibrating controller 130 and/or position sensing system 50 apply to various types of magnets 60 and configurations of magnet 60 and sensing system 50.

FIG. 6A shows a graph 200 where the horizontal and vertical axes represent a distance (in mm) from a center of a circular cross-section of magnet 60. For example, FIG. 6A may depict a magnetic field 210 of magnet 60 at a location of one or more magnetic field sensing elements 52a, 52b, 52c. The shaded regions depict regions of different strength of magnetic field 210, as shown in the key 220 on the right side of FIG. 6A. The arrows depict a direction of the magnetic field. Rectangle 230 represents one or more magnetic field sensing elements 52a, 52b, 52c. For example, rectangle 230 may represent one magnetic field sensing element 52a or two magnetic field sensing elements 52a, 52b. A dashed arc 240 may depict a path of magnetic field sensing element(s) 52a, 52b, and/or 52c, relative to magnet 60.

Rectangle 230 may represent a position of magnetic field sensing element(s) 52a, 52b, and/or 52c when elevator 16 is in a raised position/configuration/orientation (e.g., a fully raised position). An end of arc 240 opposite rectangle 230 may represent a position of magnetic field sensing element(s) 52a, 52b, and/or 52c when elevator 16 is in a lowered position/configuration/orientation (e.g., a fully lowered position). A distance between top of magnet 60 in FIG. 4B and magnetic field sensing element(s) 52a, 52b, and/or 52c may be approximately 4.6 mm (along the z-axis of FIG. 4B) in the configuration of distal assembly shown in FIGS. 1A-4C. Magnetic field sensing element(s) 52a, 52b, and/or 52c may be offset from magnet 60 by approximately 1 mm in a y-direction of FIG. 4B). However, any alternative distance may be utilized, and a distance need not remain constant.

FIG. 6B shows a diagram 250 with magnet 60 rotated to show a magnetic field 260 of magnet 60 when elevator 16 is in an intermediate position/configuration/orientation, between a fully raised and fully lowered configuration. The shaded regions depict regions of different strength of magnetic field 260 (as shown in the key 220 on the right side of FIG. 6A). The arrows depict a direction of the magnetic field. Key 220 also applies to diagram 250. Rectangle 270 represents one or more magnetic field sensing elements 52a, 52b, 52c. For example, rectangle 270 may represent one magnetic field sensing element 52a or two magnetic field sensing elements 52a, 52b. A dashed arc 280 may depict a path of magnetic field sensing element(s) 52a, 52b, and/or 52c, relative to magnet 60. Although magnetic field 260 is rotated relative to magnetic field 210, arcs 240 (FIG. 6A) and 290 (FIG. 6B) may traverse the same portions of a field of magnet 60. FIG. 6A may represent a position of magnet 60 at a first time, and FIG. 6B may represent a position of magnet at a second time. Rectangle 230 may represent a position of one or more magnetic field sensing elements 52a, 52b, 52c at the first time, and rectangle 270 may represent a position of one or more magnetic field sensing elements 52a, 52b, 52c at the second time.

A computer modeling software (e.g., MATLAB and/or Python) may be used to determine a magnetic field measured by one or more of magnetic field sensing elements 52a, 52b, 52c along arcs 240, 280. This information may be utilized in order to interpret a signal received by one or more of magnetic field sensing elements 52a, 52b, 52c during operation of device 100, including distal tip assembly 10. For example, controller 130 may be programmed with information that correlates a reading from one or more of magnetic field sensing elements 52a, 52b, 52c with a position of elevator 16.

In an example, arcs 240 (FIG. 6A) and 280 (FIG. 6B) may each depict a path of magnet 60 having axis B of magnet 60 offset from primary sensing direction C of magnetic field sensing elements 52a, 52b by approximately 0 degrees when elevator 16 is in a fully raised configuration. In a fully lowered configuration of elevator 16, axis B of magnet 60 may be offset from primary sensing direction C of magnetic field sensing elements 52a, 52b by approximately 63 degrees. The angles provided above are merely exemplary, and any suitable angles may be utilized.

In an example, as shown in FIGS. 6A and 6B, a magnetic field of elevator 16 may be stronger at a position of magnetic field sensing elements 52a, 52b when elevator 16 is in a fully lowered position than when elevator 16 is in a fully raised position. However, an angle between the magnetic field and magnetic field sensing element(s) 52a, 52b also may change as elevator 16 moves from a fully raised configuration to a fully lowered configuration. Because an angle between axis B of magnet 60 and sensing direction C of magnetic field sensing elements 52a, 52b may be smaller in the fully raised configuration (e.g., approximately 0 degrees) than in the fully lowered configuration (e.g., approximately 63 degrees), a component of the magnetic field of magnet 60 along sensing direction C may be greater in the fully raised configuration than in the fully lowered configuration. In other words, sensing direction C may be more aligned with the magnetic field of magnet 60 in the raised configuration than in the lowered configuration.

Figure 7:
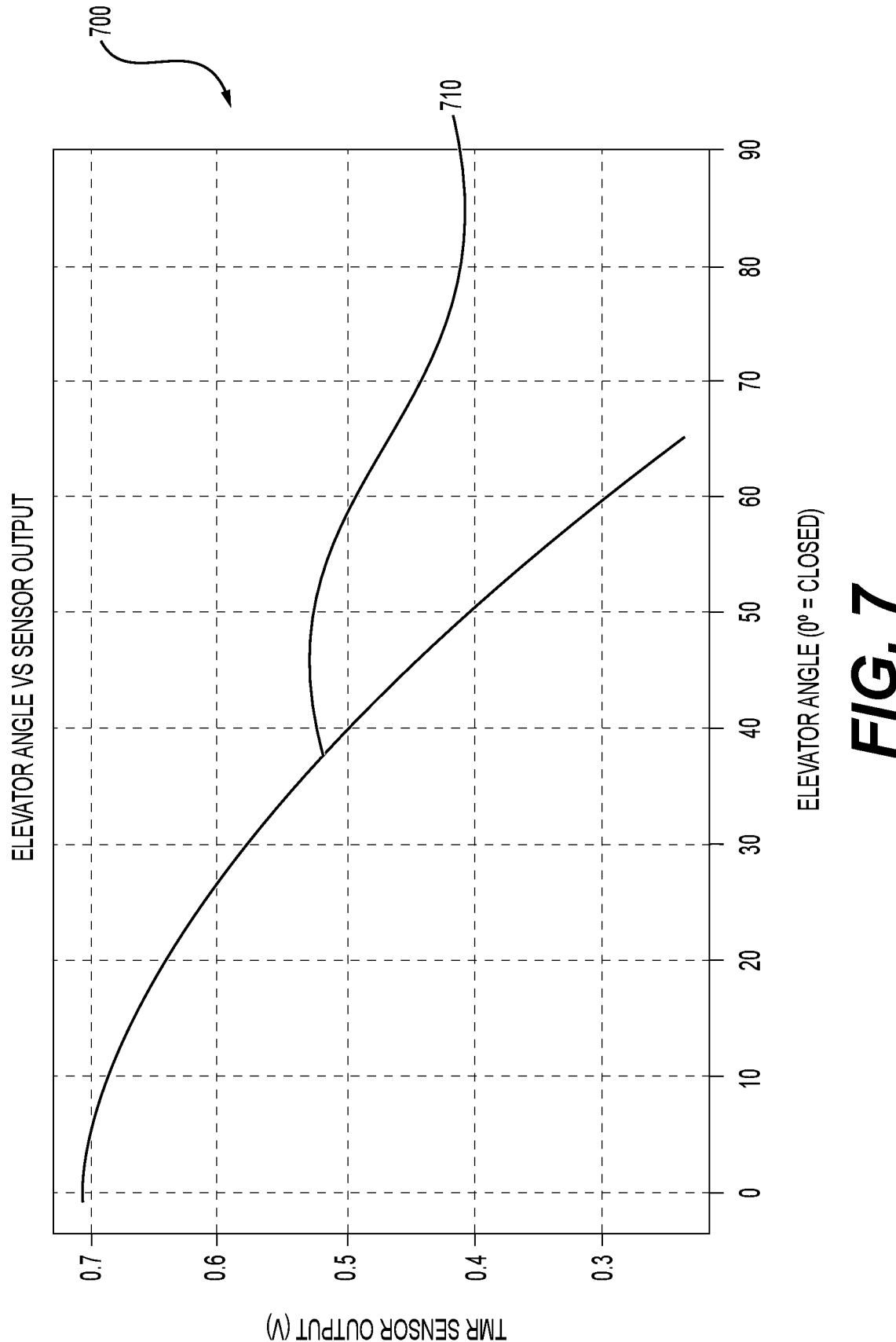
FIG. 7 depicts an exemplary expected output from a position sensing system of the exemplary distal tip of FIGS. 1A-1C.

FIG. 7 depicts a graph 700 showing an output 710 of one or more of magnetic field sensing elements 52a, 52b, 52c (in Volts) versus an angle of elevator 16 (where zero degrees is a fully raised/closed position of elevator 16). As discussed above, in one example, the output 710 shown in FIG. 7 may be an output of magnetic field sensing elements 52a, 52b. Although two magnetic field sensing elements 52a, 52b are referred to above and below, use of two magnetic field sensing elements 52a, 52b is merely exemplary however, and any suitable number (as few as one magnetic field sensing element 52a) may be utilized. In the example described above, at a location of magnetic field sensing elements 52a, 52b, a strength (i.e., a magnitude) of a magnetic field may be greater when elevator 16 is in a fully lowered configuration than when elevator 16 is in a fully raised configuration. However, as discussed above, magnetic field sensing elements 52a, 52b only measure magnetic fields along their sensing direction C. Because, as also discussed above, a vector component of the magnetic field of magnet 60 along sensing direction C may be greater in the fully raised configuration than in the fully lowered configuration, magnetic field sensing elements 52a, 52b may actually measure a greater magnitude of the magnetic field in the fully raised configuration than in the fully lowered configuration. This is because the magnetic field is more aligned with sensing direction C in the fully raised configuration than in the fully lowered configuration.

An output 710 expected from magnetic field sensing elements 52a, 52b may be calculated by multiplying a vector component of the magnetic field that aligns with sensing direction C by a linear sensitivity (which may be a known value) of magnetic field sensing elements 52a, 52b. As shown in FIG. 7, output 710 (e.g., a voltage) from magnetic field sensing elements 52a, 52b may be greatest in the fully raised configuration of elevator 16, and a voltage from magnetic field sensing elements 52a, 52c may be smallest in the fully lowered configuration of elevator 16. A signal response of magnetic field sensing elements 52a, 52b may be non-linear. A signal response of magnetic field sensing elements 52a, 52b (or other combinations of magnetic field sensing elements) may be modeled in order to make design choices for optimal measurements.

Prior to using medical device 100, including position sensing system 50, controller 130 and/or position sensing system 50 may be calibrated. For example, as discussed above with respect to FIGS. 6A-6B, a magnetic field (including magnitude and direction) of magnet 60 at various relative locations of magnetic field sensing elements 52a, 52b, and/or 52c may be determined. As discussed with respect to FIG. 7, a response of magnetic field sensing elements 52a, 52b, and/or 52c to the various magnetic fields may be determined. The determined responses may be used to interpret a signal from position sensing system 50 during a procedure. Based on a signal of magnetic field sensing elements 52a, 52b, and/or 52c, the magnetic field of magnet 60 and/or position of elevator 16 may be determined.

Medical device 100, including distal tip assembly 10, may be used to perform a medical procedure on a subject. The procedure may be performed robotically and/or by a human operator. For example, medical device 100 may be inserted into a body lumen (e.g., a duodenum) of a subject. During the procedure, an external device may be used to generate a magnetic field near the subject. The generated magnetic field may be, for example, an alternating magnetic field (e.g., at a 1250 Hz frequency). For example, the external device may be positioned on a table or other surface near the subject (e.g., near the part of the body where the body lumen is located). An operator may actuate actuator 112 to adjust a position of elevator 16.

During the procedure, position sensing system 50 (including magnetic field sensing elements 52a, 52b, 52c) may transmit signals through shaft 114, to handle 110, and through umbilicus 132 to controller 130. The signals from position sensing system 50 may indicate a position and/or orientation of distal tip 118 (including distal tip assembly 10) within the body. The signals from position sensing system 50 may also indicate a position of elevator 16.

As discussed above, one or more magnetic field sensing elements 52a, 52b, 52c may be capable of measuring static magnetic fields. Although elevator 16 may move, a magnetic field emitted by magnet 60 may be essentially static, as compared to the alternating magnetic fields of the external magnetic field-generating device, discussed above. Thus, one or more magnetic field sensing elements 52a, 52b, 52c may be able to simultaneously measure the alternating external field and the static field of magnet 60. For example, controller 130 may be programmed to separate an output from magnetic field sensing elements 52a, 52b, 52c into components related to (a) the external, alternating magnetic field and (b) elevator 16. Controller 130 may also be programmed to identify and filter out portions of an output from magnetic field sensing elements 52a, 52b, 52c that are due to Earth's magnetic field. Thus, controller 130 may determine, based on an output from magnetic field sensing elements 52a, 52b, 52c, a position and/or orientation of distal tip assembly 10, and/or a position of elevator 16.

Position and/or orientation information of distal tip assembly 10 and/or information about a position of elevator 16 may be fused with imaging (e.g., 3D imaging) performed before the procedure. For example, position-sensing system 50 may enable use of an augmented camera view or an augmented three-dimensional ("3D") view in which an operator may see a trajectory of the instrument, a location of the papilla, and/or a trajectory of the bile duct in real time, and/or in the same coordinate system. The position-sensing system may assist cannulation of the papilla with minimal changes to a current ERCP workflow. Information from position sensing system 50 may provide an operator with information about anatomy near device 100, which camera 32 alone may be unable to visualize (including anatomy outside of the body lumen in which device 100 is disposed). For example, position sensing system 50 may provide information regarding common and pancreatic bile ducts through a wall of the duodenum. Position sensing system 50 may assist positioning of distal tip assembly 10 and positioning of an instrument with elevator 16, in order to facilitate cannulation of the papilla and/or performing procedures with the instrument.

Furthermore, pre-procedure images may be used to automatically segment a mesh of the anatomy so as to provide a map (e.g., a 3D map) to track medical device 100 in real time. Such real-time tracking may decrease the amount of time, skill, and/or effort required to reach a target anatomy. In the absence of pre-procedure images, position sensing system 50 may enable software to track a position of device 100 and movements of device 100, in order to generate a map (e.g., a 3D map) in real time, during the procedure. The generated map may guide medical device 100 (and any EM-enabled accessories) through the subject's anatomy. Medical device 100 may be utilized with any techniques that are known or become known, including MR image fusion, preoperative CT image fusion, electromagnetic (EM) tracking, artificial intelligence-based automatic tissue segmentation, augmented reality, 3D visualizations, and/or a fully robotic-controlled endoscope.

Controller 130 may include a display or may transmit a signal to an external display (not shown). The display may present information to an operator about the position and/or orientation of distal tip assembly 10 and/or the position of elevator 16. For example, the display may present 3D views and/or virtual reality views to the operator. The display also may present information about a position of elevator 16. For example, the display may present information about an angle of elevator 16 and/or a relative position between the instrument and the papilla or other structure.

Figure 8:
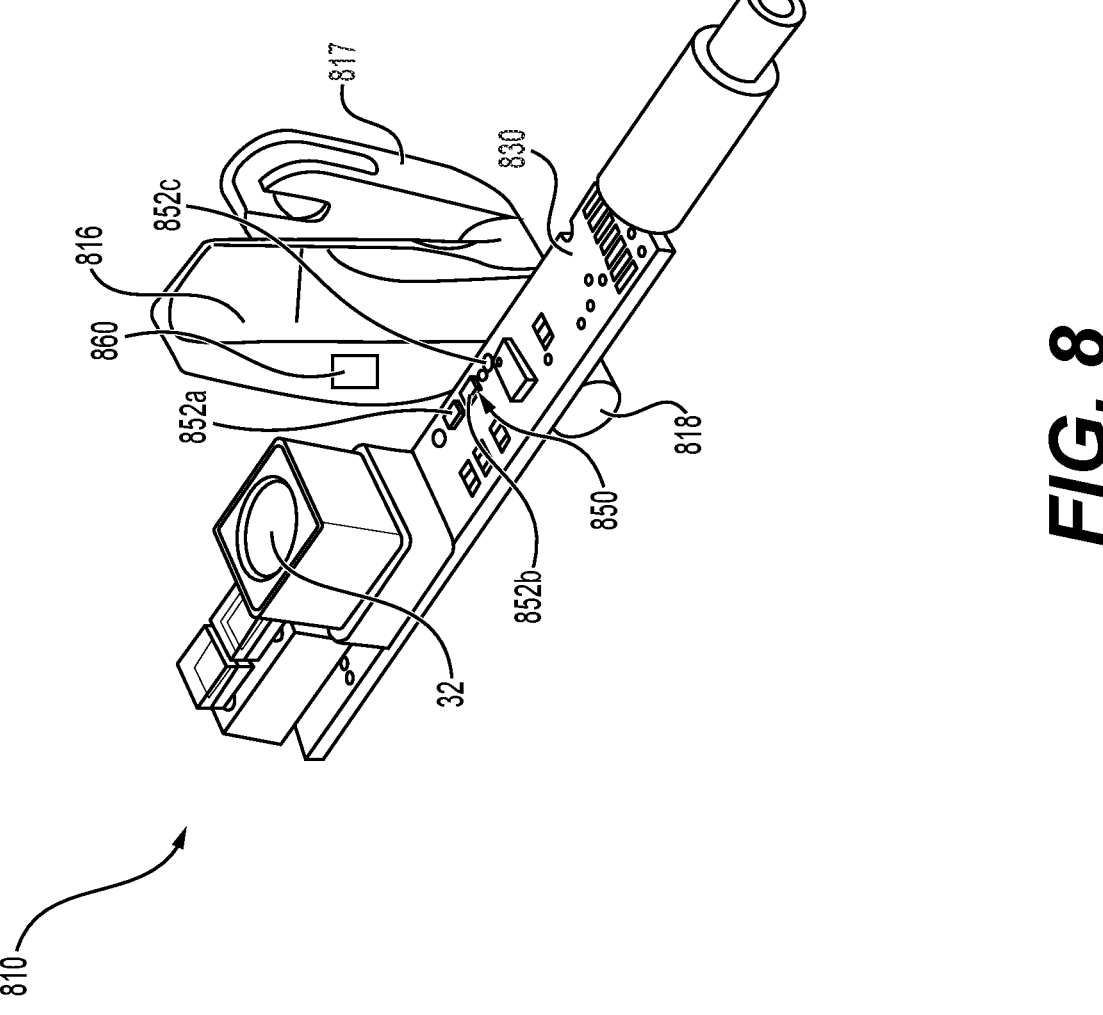
FIG. 8 depicts an elevator and electronic components of an alternative distal tip.

FIG. 8 shows elements of an alternative distal tip assembly 810, which, except as specified below, may include any of the properties of distal tip assembly 10. Although elements such as core 12 and cover 14 are not depicted, it will be appreciated that distal tip assembly 810 may include such elements, as well as others depicted and/or discussed with respect to distal assembly 10. Distal tip assembly 810 may include an elevator 816, which may include any of the features of elevator 16, except as specified herein. Elevator 816 may have an elevator sensor 860 coupled thereto. Elevator sensor 860 may include, for example, any type of gyroscopic sensor, including, by way of example, an inertial measurement unit. Elevator sensor 860 may be positioned on any suitable location of elevator 816, such as on a side of elevator 816 (as shown in FIG. 8), on an axle 818 of elevator 816, or on a lever arm 817 of elevator 816. Elevator sensor 860 may be coupled (e.g., mechanically coupled) to elevator 816, encapsulated within elevator 816, or otherwise disposed on or within elevator 816.

A substrate 830 may have a position sensing system 850 mounted thereon. Position sensing system 850 may include a plurality of sensing elements 852a, 852b, 852c having any suitable position/configuration on substrate 830 (or another element of distal tip assembly 810). Sensing elements 852a, 852b, 852c may include, for example, accelerators and/or gyroscopic sensors. Although three sensing elements 852a, 852b, 852c are depicted, any suitable number and arrangement of sensing elements may be utilized (including fewer or more sensors). Sensing elements 852a, 852b, and/or 852c may generate signals indicative of a position/orientation of distal tip assembly 810 (e.g., of substrate 860).

A controller (e.g., controller 130) may have functionality to analyze an output from position sensing system 850 and/or elevator sensor 860. For example, controller 130 may determine what component(s) of a signal from elevator sensor 860 are attributable to movement of an entirety of distal tip assembly 810, rather than from elevator 816 alone. In examples, data from sensing elements 852a, 852b, and/or 852c may be used in order to identify movement of an entirety of distal tip assembly 810. Controller 130 may be programmed with algorithms to negate movement of an entirety of distal tip, determining which movement identified by elevator sensor 860 is due to raising/lowering of elevator 816 (i.e., independent movement of elevator 816 relative to elements such as substrate 830 and the components mounted thereon), rather than due to movement of distal tip assembly 810 as a whole. As compared with use of distal tip assembly 10, use of distal tip assembly 810 may not involve generation of an external magnetic field.

Because elevator sensor 860 and/or position sensing system 850 may measure only acceleration (which is used to approximate displacement), a cumulative error may accrue. Distal tip assembly 810 may periodically be calibrated in order to compensate for the cumulative error. For example, calibration may set a baseline measurement value of a known position. In an example, to calibrate elevator sensor 860, an operator could fully raise (or fully lower) elevator

816. An additional sensor (not depicted) may indicate (e.g., provide an indicative signal) when elevator 816 is fully raised (or fully lowered). Additionally or alternatively, an operator could press a button to confirm that elevator 816 is fully raised (or fully lowered) in order to calibrate (e.g., "zero") the position of elevator sensor 860. In an example, to calibrate position sensing system 850 of substrate 830, software (e.g., of controller 130) may correlate information shown by camera 32 to, for example, 1) information previously mapped in a three-dimensional coordinate system (which may be produced from a simultaneous localization and mapping ("SLAM") or another algorithm) and/or 2) information obtained from a pre-operative image, such as a computed tomography ("CT") or magnetic resonance imaging ("MRI") scan.

Any methods or portions of methods described in this disclosure may be performed by one or more processors of a computer system (e.g., of controller 130). The one or more processors may be configured to perform such methods by having access to instructions (e.g., software or computer-readable code) that, when executed by the one or more processors, configure and/or cause the one or more processors to perform the methods. Such instructions may be stored in a memory of the computer system.

Instructions executable by one or more processors may also be stored on a non-transitory computer-readable medium. Therefore, whenever a computer-implemented method is described in this disclosure, this disclosure shall also be understood as describing a non-transitory computer-readable medium storing instructions that, when executed by one or more processors of a computer system, configure and/or cause the one or more processors to perform the computer-implemented method. Examples of non-transitory computer-readable media include RAM, ROM, solid-state storage media (e.g., solid state drives), optical storage media (e.g., optical discs), and magnetic storage media (e.g., hard disk drives). A non-transitory computer-readable medium may be part of the memory of a computer system or separate from any computer system.

A computer system may include one or more computing devices. If a computer system includes a plurality of processors, the plurality of processors may be included in a single computing device or distributed among a plurality of computing devices. A processor may be a central processing unit (CPU), a graphics processing unit (GPU), or another type of processing unit. The term "computational device," as used in this disclosure, is interchangeable with "computing device." An "electronic storage device" may include any of the non-transitory computer-readable media described above.

While principles of this disclosure are described herein with the reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. An assembly of a medical device, the assembly comprising:
   an elevator configured to raise and lower in order to adjust an orientation of an instrument inserted through a working channel of the medical device, wherein the elevator includes a magnet; and a sensing element configured to measure a magnetic field of the magnet and to output a signal indicative of a configuration of the elevator, wherein the sensing element includes a magnetoresistive sensor, wherein an axis of the magnet is configured to be offset from a sensing direction of the magnetoresistive sensor by a first amount in a first configuration of the elevator, wherein the sensing element is configured to measure a component of the magnetic field of the magnet that is along a sensing direction of the magnetoresistive sensor, and wherein the axis of the magnet is configured to be offset from the sensing direction of the magnetoresistive sensor by a second amount in a second configuration of the elevator.

2. The assembly of claim 1, wherein the magnet is diametrically magnetized.

3. The assembly of claim 1, wherein the magnet is disposed in a recess of an axle of the elevator.

4. The assembly of claim 1, wherein the magnet is cylindrical.

5. The assembly of claim 1, wherein the magnet rotates about a longitudinal axis of the magnet as the elevator is raised and lowered.

6. The assembly of claim 1, wherein the sensing element is further configured to generate a signal indicative of an orientation of a distal tip of the medical device.

7. The assembly of claim 6, wherein the sensing element is configured to measure an alternating external magnetic field in order to output the signal indicative of the orientation of the distal tip.

8. The assembly of claim 7, wherein the sensing element is configured to measure a static magnetic field of the magnet.

9. The assembly of claim 1, wherein the sensing element is mounted on a substrate of a distal tip of the medical device.

10. The assembly of claim 1, wherein the magnet is a permanent magnet.

11. The assembly of claim 1, wherein the sensing element is a first sensing element, the assembly further comprising a second sensing element configured to measure a magnetic field of the magnet.

12. The assembly of claim 1, wherein the sensing element is configured to measure a different magnitude of the magnetic field in a fully-raised configuration of the elevator than in a fully-lowered configuration of the elevator.

* * * * *